United States Patent
Chen

(10) Patent No.: US 10,147,319 B1
(45) Date of Patent: Dec. 4, 2018

(54) SAFE DRIVING SYSTEM HAVING FUNCTION OF DETECTING HEART RATE VARIABILITY

(71) Applicant: Pin-Hua Chen, Kaohsiung (TW)

(72) Inventor: Pin-Hua Chen, Kaohsiung (TW)

( * ) Notice: Subject to any disclaimer, the term of this patent is extended or adjusted under 35 U.S.C. 154(b) by 0 days.

(21) Appl. No.: 15/852,243

(22) Filed: Dec. 22, 2017

(51) Int. Cl.
| | |
|---|---|
| G08G 1/00 | (2006.01) |
| G08G 1/0965 | (2006.01) |
| G08G 1/123 | (2006.01) |
| G08G 1/052 | (2006.01) |
| G08B 21/04 | (2006.01) |
| H04W 4/90 | (2018.01) |
| H04W 4/40 | (2018.01) |
| B60C 9/00 | (2006.01) |
| A61B 5/024 | (2006.01) |
| A61B 5/18 | (2006.01) |

(52) U.S. Cl.
CPC ............ *G08G 1/0965* (2013.01); *B60C 9/00* (2013.01); *G08B 21/0453* (2013.01); *G08G 1/052* (2013.01); *G08G 1/123* (2013.01); *H04W 4/40* (2018.02); *H04W 4/90* (2018.02); *A61B 5/02405* (2013.01); *A61B 5/18* (2013.01)

(58) Field of Classification Search
CPC ...... G08G 1/0965; G08G 1/052; G08G 1/123; B60Q 9/00; H04W 4/40; H04W 4/90; G08B 21/0453; A61B 5/18; A61B 5/02405

USPC ........ 340/902, 903, 438, 439, 435, 436, 457
See application file for complete search history.

(56) References Cited

U.S. PATENT DOCUMENTS

| | | | | |
|---|---|---|---|---|
| 9,934,667 | B1* | 4/2018 | Fields | ..................... G08B 21/02 |
| 2015/0158425 | A1* | 6/2015 | Han | ......................... B60Q 9/00 |
| | | | | 701/41 |
| 2016/0039424 | A1* | 2/2016 | Hong | ..................... B60W 40/08 |
| | | | | 701/2 |
| 2017/0172520 | A1* | 6/2017 | Kannan | ................ A61B 5/7282 |

\* cited by examiner

*Primary Examiner* — Anh V La
(74) *Attorney, Agent, or Firm* — WPAT, PC

(57) ABSTRACT

A safe driving system having function of detecting heart rate variability is disclosed. The safe driving system having function of detecting heart rate variability mainly includes a detection display unit and a main control host. The detection display unit includes: a HRV detecting module, a display interface module, a first internal wireless communication module, a control button, a first processor, a power module and a voice management module comprising a microphone and an amplifier. The main control host includes: a mobile communication module, a satellite navigation system module, a second internal wireless communication module, a records preserving module, a second processor, a vehicle power module, a secondary power module, a power management module and an alarm module. The safe driving system having function of detecting heart rate variability is able to prevent the vehicle's driver from traffic accidents jeopardizing traffic safety due to drinking, taking drug, fatigue or an emergency occurred while driving.

23 Claims, 4 Drawing Sheets

SAFE DRIVING SYSTEM HAVING FUNCTION OF DETECTING HEART RATE VARIABILITY

FIELD OF THE INVENTION

The present invention relates to a safe driving system. More specifically, the present invention relates to a safe driving system having function of detecting heart rate variability.

BACKGROUND OF THE INVENTION

Traffic safety has always been the first priority of traffic management authorities. In order to allow drivers to drive safely and pedestrians to walk peacefully, there are many road safety propagandas appeared in daily life to remind everyone. However, most traffic fatalities are often caused by drunk driving, drug abuse, fatigue or sudden discomfort of the body so that people cannot focus on driving. The results often cause unbearable suffering for many families. Therefore, in order to solve the man-made traffic safety problems, many traffic safety aids or systems related to the traffic safety have emerged.

Conventionally, vehicles may be installed with ADAS (Advanced Driver Assistance System). The system can detect certain objects and perform a basic classification to warn the driver of the dangerous conditions on the road. Furthermore, it can slow down or stop the vehicle under some emergency situations. The ADAS can be properly used to monitor blind spots and assist in lane changes to show warnings for front impacts. However, the vehicles are still controlled by the drivers. If the driver's mental state during driving is not good, they may still be in danger of driving the vehicle without following the instructions of the ADAS. In addition, the concept of smart cars is gradually being carried out. These smart cars are capable of deep learning and application of driver habits, driving environments, and even traffic regulations. In other words, a safe driving system with relevant intelligent learning functions, in the case of familiar with the traffic conditions, can replace the driver to drive by itself. However, no matter how advanced and developed this technology will be in the future, the innate pursuit of a sense of speed by human beings and the belief that the computer system cannot be absolutely stable and error-free both make man-made driving is a necessity. Once involved in human control, the drivers' physiological and mental status are again the key to traffic safety.

From the technical point of view, the aforementioned technologies are still under development, or only with the prototypes. In addition, the governments of all countries in the world still wait and see. There is no timetable for legislation and implementation of traffic laws related to the above technologies. At this stage, there are still many available driving safety assistive technologies. In particularly, a technology which can monitor the drivers' physiological status is a revolutionary and breakthrough technology. The technology is mainly to detect the driver's Heart Rate Variability (HRV) and check if it is suitable for driving or not. HRV is the degree to which the frequency of heart beats varies over a time interval. When human's HRV at high level, they would have more attention to ignore distractions. On the contrary, human would reduce attention when their physiology or awareness was interfered. Therefore the negative emotions like anxiety, anger, melancholy etc. would reduce the HRV easily. Especially after drinking, taking drugs or being fatigue want to sleep, the HRV would decrease sharply than negative emotions caused. The above arguments have been confirmed in various scientific journals and proved by physiological experiments. The scientific journals such as "Acute alcohol ingestion reduces Heart Rate Variability", Drug and Alcohol Dependence, Elsevier Scientific Publishers Ireland Ltd., 1986; "Acute alcohol intake decreases short-term Heart Rate Variability in healthy subjects", Clinical Science, 1994; "Relations between alcohol consumption, Heart Rate, and Heart Rate Variability in men", National Institutes of Health (NIH), 2002; "Fatigue Shifts and Scatters Heart Rate Variability in Elite Endurance Athletes", National Institutes of Health (NIH), 2013 and "Heart Rate Variability and the Efficacy of Biofeedback in Heroin Users with Depressive Symptoms", The Korean College of Neuropsychopharmacology, 2016.

In practice, there are many HRV modules available for use. For example, the module "SFH 7050—Photo Plethysmoraphy (PPG) Sensor" manufactured by Osram. The device's dimensions about 4.7×2.5×0.9 (L×W×H) mm. It has a very small size and high accuracy that can make the function of detecting HRV be assembled on any portable electronic products, such as smart watches. This kind of device makes the detection of HRV become more convenient. If the module for detecting HRV could be applied to the safe driving system, it could warn drivers if their physiological status were not suitable for driving. In currently, there absolutely not have any applications which can detect HRV in safe driving systems.

Therefore, based on many years of research and development on the safe driving system of vehicles and many experiments on the physiological conditions of drivers. In practical experience in integration of hardware and software of electronic devices, the present inventor has provided the safe driving system having function of detecting HRV. It not only breaks through the limitations of existing traffic environments and driving habits at once, but also contributes great efforts to safety driving. Moreover, the safe driving system having function of detecting HRV can exert the anti-theft function by identifying the unique HRV of each person to prevent the vehicles' owners from theft events.

SUMMARY OF THE INVENTION

This paragraph extracts and compiles some features of the present invention; other features will be disclosed in the follow-up paragraphs. It is intended to cover various modifications and similar arrangements included within the spirit and scope of the appended claims.

One of the objects of the present invention is to use HRV detection techniques for safe driving, preventing drivers from jeopardizing the traffic safety due to drinking, taking drug, fatigue driving or driving in an emergency situation. Therefore, a safe driving system having a function of detecting HRV is disclosed. It includes: a detection display unit, comprising: a HRV (Heart Rate Variability) detecting module, for detecting and outputting a HRV value of a vehicle driver, and when the detected HRV value fallen into a predetermined abnormal value range, sending out a corresponding warning message; a display interface module, for displaying the warning message or a light or a text corresponding to the warning message; a first internal wireless communication module, for sending and receiving wireless signals; a control button, touched to control the display interface module and sending out an emergency message; a first processor, connected to the HRV detecting module, the display interface module, the first internal wireless communication module and the control button, for operating said connected objects, and sending out the warning message, the emergency message and records of HRV via the first internal wireless communication module; a power module, for providing power required for operation to the HRV detecting module, the display interface module, the first internal wireless communication module, the control button, and the first processor; and a power module, for providing the power for the operation of the HRV detecting module, the display interface module, the first internal wireless communication module, the control button, the first processor and the voice management module; and a main control host, comprising: a mobile communication module, installed with a SIM (Subscriber Identity Module), for sending and receiving messages through a mobile network; a satellite navigation system module, for receiving satellite signals to calculate location and speed information of the main control host; a second internal wireless communication module, paired with and wirelessly connected to the first internal wireless communication module, for sending and receiving wireless signals; a storing module, for storing HRV values patterns of a vehicle owner and a plurality of users authorized by the vehicle owner to use the vehicle, at least one mobile phone number, a vehicle identification number of the vehicle, and a plurality of newest recorded HRV values from the first internal wireless communication module; and a second processor, connected to the mobile communication module, the satellite navigation system module, the second internal wireless communication module and the storing module, for operating said connected objects, judging if a data is stored in the storing module, and sending out the warning message, the emergency message, the location and speed information and the vehicle identification number from the first internal wireless communication module to a specific external receiver via the mobile communication module; a vehicle power module, connected to a power supply of the vehicle; a secondary power module, for storing and supplying power; and a power management module, connected to the mobile communication module, the satellite navigation system module, the second internal wireless communication module, the storing module, the second processor, the vehicle power module, the secondary power module and alarm module, for controlling the power from the vehicle power module for the operation of each module in the main control host, and providing the power from the secondary power module to maintain the operation of the main control host when an abnormal power failure occurs between the vehicle power module and the power supply of the vehicle.

According to the present invention, the detection display unit may further comprise: a voice management module, connected to the first processor, for sending out and receiving voice messages, comprising: a microphone, for converting voice into digital data, and sending out the digital data externally via the first processor, the first internal wireless communication module, the second internal wireless communication module, the second processor and the mobile communication module; and an amplifier, for converting digital data sent from the mobile communication module, through the second processor, the second internal wireless communication module, the first internal wireless communication module and the first processor into voice and amplifying the voice.

Preferably, the detection display unit may be able to make or answer a phone call through the mobile communication module of the main control host, and input and receive voice through the voice management module.

Preferably, the first processor may utilize the HRV value of the vehicle driver detected by the HRV detecting module to judge if the driver is suitable for driving or not, and inform the driver about the result of judgment through the amplifier of the voice management module.

Preferably, the predetermined abnormal value range is a range of HRV values measured from human experiments under fatigue, lack of sleep, taking drug, drinking or acute illness resulting in inability to drive the vehicle properly.

Preferably, the first internal wireless communication module and the second internal wireless communication module may be Bluetooth modules or NFC (Near Field Communication) modules.

Preferably, the warning message and the vehicle identification number may be sent to the police department reporting system, a specific transceiver of patrol police officers or a mobile device installed with an APP interpreting the warning message and the vehicle identification number.

According to the present invention, the main control host may further comprise an alarm module capable of making alarming sounds. The alarm module makes the alarming sounds of 30 seconds to warn the driver that an abnormality has occurred in the detection display unit when the main control host detects no detection display unit for pairing.

Preferably, the second processor further judges if the second internal wireless communication module and the first internal wireless communication module paired and connected. When the second processor judges the second internal wireless communication module and the first internal wireless communication module are not paired and connected, the second internal wireless communication module keeps sending pairing signals. At this moment, if the patrol police officer approaches the vehicle with a specific transceiver capable of receiving the pairing signal, the specific transceiver would be paired with the main control host. The patrol police officer would be aware of the vehicle's detection display unit device is abnormal and check it out what happened. If paring and connecting are not finished within 30 seconds, the second processor sends out an alert message to the vehicle owner or the police via the mobile communication module. If paring and connecting are finished within 30 seconds, the HRV detecting module waits for 15 seconds for the driver to process HRV detecting.

Preferably, if the driver processes HRV detecting within 15 seconds, the first processor judges whether the HRV value falls into the predetermined abnormal value range, and the second processor judges if the pattern of the HRV values is different from that of the vehicle owner and a plurality of users authorized by the vehicle owner in the storing module; if the driver doesn't processes HRV detecting within 15 seconds, the first processor further initiates a 5-minutes countdown.

Preferably, if the HRV value doesn't fall into the predetermined abnormal value range, the display interface module displays a normal detection message, and the HRV detecting module processes another HRV detecting within 30 minutes to the driver to judge if the HRV value falls into the predetermined abnormal value range.

Preferably, if the HRV value falls into the predetermined abnormal value range, a reason of the HRV value fallen into the predetermined abnormal value range caused by drinking, fatigue or taking drug is judged by the first processor through the HRV detecting module.

Preferably, if the HRV value fallen into the predetermined abnormal value range is caused by drinking, the HRV detecting module sends out a drunk driving warning message to display on the display interface module to warn the driver to stop by the roadside and shut down the engine, the alarm module makes alarming sounds every 5 minutes, and the drunk driving warning message is passed to the second internal wireless communication module via the first internal wireless communication module, further sent to the police reporting system, a specific transceiver of patrol police officers within 5 meters around the vehicle, or a mobile device installed with an APP interpreting the drunk driving warning message and the vehicle identification number along with the location of the vehicle and the vehicle identification number through the second processor and the mobile communication module.

Preferably, if the HRV value fallen into the predetermined abnormal value range is caused by fatigue, the HRV detecting module sends out an fatigue driving warning message to display on the display interface module to warn the driver to stop by the roadside and shut down the engine, the alarm module makes alarming sounds every 5 minutes, and the fatigue driving warning message is passed to the second internal wireless communication module via the first internal wireless communication module, further sent to the police reporting system, a specific transceiver of patrol police officers within 5 meters around the vehicle, or a mobile device installed with an APP interpreting the fatigue driving warning message and the vehicle identification number along with the location of the vehicle and the vehicle identification number through the second processor and the mobile communication module.

Preferably, if the HRV value fallen into the predetermined abnormal value range is caused by taking drug, the HRV detecting module sends out an drug taking warning message to display on the display interface module to warn the driver to stop by the roadside and shut down the engine, the alarm module makes alarming sounds every 5 minutes, and the drug taking warning message is passed to the second internal wireless communication module via the first internal wireless communication module, further sent to the police reporting system, a specific transceiver of patrol police officers within 5 meters around the vehicle, or a mobile device installed with an APP interpreting the drug taking warning message and the vehicle identification number along with the location of the vehicle and the vehicle identification number through the second processor and the mobile communication module.

Preferably, f any one HRV value is detected by the HRV detecting module within the 5-minutes countdown, the first processor stops the 5-minutes countdown, and the HRV detecting module judges if the HRV value falls into the predetermined abnormal value range or not.

Preferably, if no HRV value is detected by the HRV detecting module within the 5-minutes countdown, the HRV detecting module sends out a no-HRV-detected driving warning message to display on the display interface module to warn the driver to stop by the roadside and shut down the engine, the alarm module makes alarming sounds every 1 minute, the no-HRV-detected driving warning message is passed to the second internal wireless communication module via the first internal wireless communication module, further sent to the police reporting system or a specific transceiver of patrol police officers within 5 meters around the vehicle along with the location of the vehicle and the vehicle identification number through the second processor and the mobile communication module.

According to the architecture above, the safe driving system having function of HRV is able to prevent the driver from traffic accidents jeopardizing traffic safety due to drinking, taking drug, fatigue or an emergency occurred while driving.

Therefore, if the pattern of the driver's HRV values is different from that of the vehicle owner and a number of users authorized by the vehicle owner in the storing module, the HRV detecting module sends out an unauthorized driving warning message to display on the display interface module to warn the driver of non-authorization, and the unauthorized driving warning message is passed to the second internal wireless communication module via the first internal wireless communication module, further sent to a mobile device of the vehicle owner and a specific transceiver of patrol police officers within 5 meters around the vehicle. If the vehicle is indeed stolen, the vehicle's position can be obtained by the vehicle owner and the police. In addition, the vehicle owner can also talk to the driver through the voice management module of the detection display unit and identifies who the driver is to clarify whether the vehicle is stolen.

Another object of the present invention is to prevent the driver from casualties and accidents when the driver suddenly feels uncomfortable and unable to drive the vehicle well. It is able to urgently call 119 for help. Therefore, if the control button is pressed over 8 seconds, the first processor sends out an emergency message, and the emergency message is passed to the second internal wireless communication module via the first internal wireless communication module, further sent to the fire department reporting system, a specific transceiver of patrol police officers within 5 meters around the vehicle, or a mobile device installed with an APP interpreting the emergency message and the vehicle identification number along with the location of the vehicle and the vehicle identification number through the second processor and the mobile communication module.

Last, still another object of the present invention is a function of speeding warning. The second processor can utilize received location information to calculate the speed of the vehicle after the engine of the vehicle is initiated. If the second processor finds that the speed of the vehicle is higher than a maximum speed limit of a road where the vehicle runs to a certain percentage and the speed of the vehicle keeps for more than 20 seconds, the second processor sends out an speeding violation message, the location of the vehicle, the speed of the vehicle and the vehicle identification number to the police reporting system or a specific transceiver of patrol police officers within 5 meters around the vehicle via the mobile communication module, and stores details of speeding in the storing module. Thus, drivers are not able to be arbitrarily speeding.

DETAILED DESCRIPTION OF THE PREFERRED EMBODIMENTS

The present invention will now be described more specifically with reference to the following embodiments.

Figure 1:
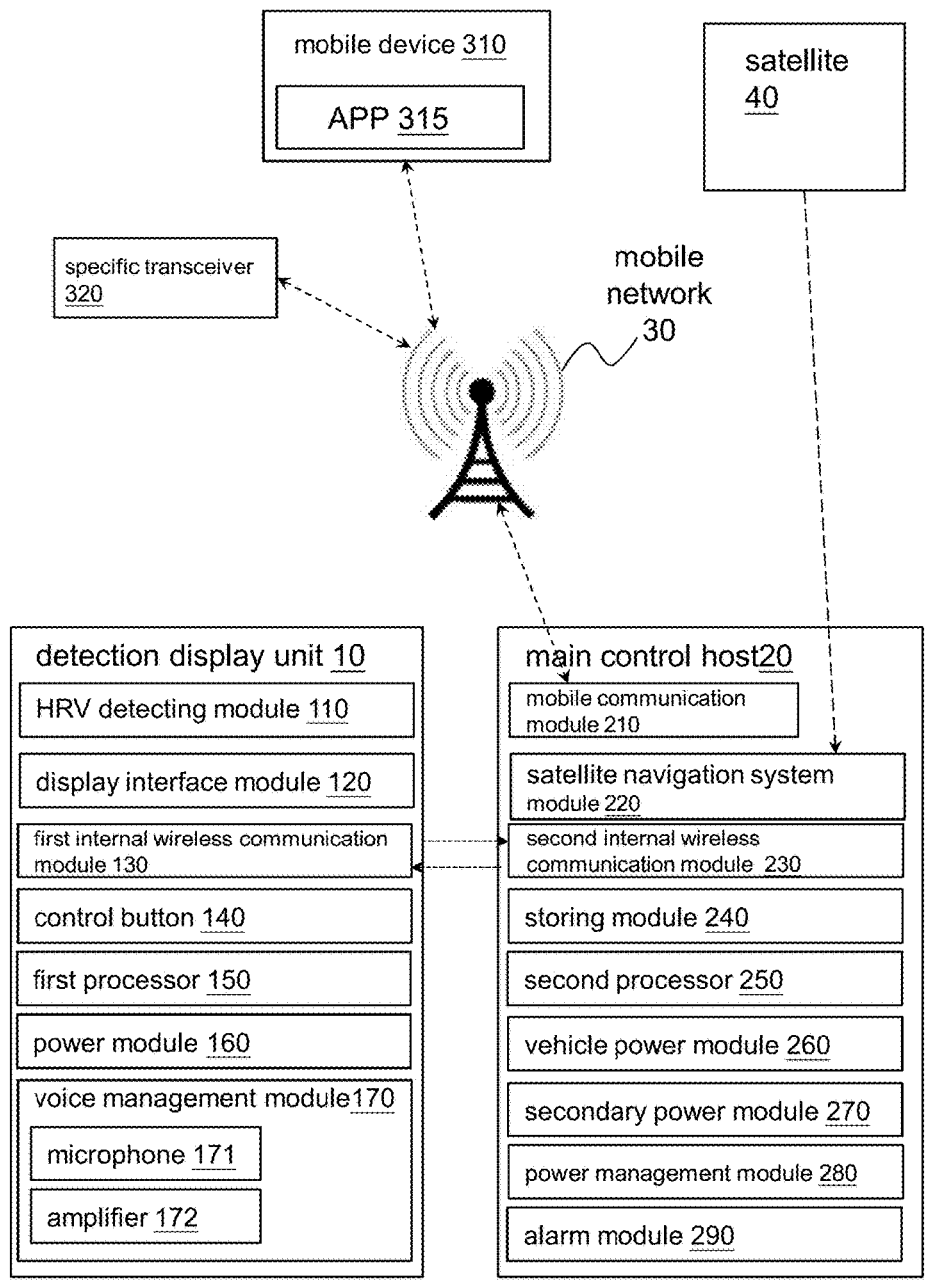
FIG. 1 shows a block diagram of a safe driving system having a function of detecting HRV disclosed by the present invention.

Please refer to FIG. 1. It shows a block diagram of a safe driving system having a function of detecting HRV disclosed by the present invention. The safe driving system having a function of detecting HRV is composed of a detection display unit 10 and a main control host 20. In practice, a vehicle equipped with the safe driving system having a function of detecting HRV has one main control host 20. However, for safety and operational considerations, the number of the detection display unit 10 may be more than one. The detection display unit 10 includes a HRV detecting module 110, a display interface module 120, a first internal wireless communication module 130, a control button 140, a first processor 150, a power module 160 and a voice management module 170. The main control host 20 includes a mobile communication module 210, a satellite navigation system module 220, a second internal wireless communication module 230, a storing module 240, a second processor 250, a vehicle power module 260, a secondary power module 270, a power management module 280 and an alarm module 290. Functions of the aforementioned elements and operation of the safe driving system having a function of detecting HRV are described in detail below.

HRV detecting module 110 is a modular circuit, used for detecting and outputting a HRV value of a vehicle driver. The HRV detecting module 110 is not large in size and suitable for a finger to put thereon to detect HRV. In addition, the HRV detecting module 110 can also send out a corresponding warning message when the detected HRV value fallen into a predetermined abnormal value range. The so-called predetermined abnormal value range is a range of HRV values measured from human experiments under fatigue, lack of sleep, taking drug, drinking or acute illness, such as myocardial infarction, resulting in inability to drive the vehicle properly. In fact, the range may cover extreme measured HRV values. Preferably, the predetermined abnormal value range may be further a shrunk range obtained after processing statistics and precision calculations over the measured HRV values. In other words, normal HRV values fall outside the predetermined abnormal value range. Each body condition which is not good for driving has a corresponding predetermined abnormal value range. The spirit of the present invention is to use the detected different HRV to remind the driver, the public around and the police and note that there may be traffic incidents, even processing anti-theft function to protect the vehicle. Here, the warning message may be a paragraph of text, images, displayed light signals or a mixture thereof. Content of the warning message can be adjusted according to different purposes. For example, if a reason of abnormal HRV value detected by the HRV detecting module 110 is drinking, a drunk driving warning message will be sent out. The content of the drunk driving warning message indicates the driver drinks much before or during driving and asks the driver to stop by the roadside and shut down the engine.

The display interface module 120 is used to display said warning message or a light or a text corresponding to the warning message. In practice, the display interface module 120 may be a liquid crystal display for displaying texts, images, or even lights for the warning message. The display interface module 120 may also be a display light group, such as a light group of red, yellow and green lights. Each light is set to represent a kind of warning. For example, a red light turns on to show a text of "please stop driving due to drinking" on a transparent sticker over the light group.

Functions of the first internal wireless communication module 130 are to send and receive wireless signals. The first internal wireless communication module 130 and the second internal wireless communication module 230 are modules of the same functions. For example, they may be Bluetooth modules or NFC (Near Field Communication) modules. They can pair and connect without being interfered externally so that the detection display unit 10 and the main control host 20 are interactively communicated.

The control button 140 can be touched to control the display interface module 120. For example, when the display interface module 120 is controlled to display the warning message showing the driver's health is abnormal, the control button 140 can switch displayed messages. In addition, according to the spirit of the present invention, the control button 140 can send out an emergency message to help the driver when his body is in a critical condition and cannot continue to drive the vehicle normally. The driver can immediately call for help. The warning message, the emergency message, the position of the vehicle, the speed of the vehicle and the vehicle identification number can be sent to the police or fire department reporting system, a specific transceiver of patrol officers, a mobile device of the vehicle owner, or a mobile device installed with an APP interpreting the warning message, the emergency message and the vehicle identification number. Functional operation of this part will be described in detail in the text below.

The first processor 150 is connected to the HRV detecting module 110, the display interface module 120, the first internal wireless communication module 130, the control button 140 and the voice management module 170, for operating said connected objects. The first processor 150 also sends out the warning message, the emergency message and records of HRV values, via the first internal wireless communication module 130, to the second internal wireless communication module 230 for further processes. In addition, the first processor 150 can utilize the values detected by the HRV detecting module 110 to judge if the driver is suitable for driving or not and to inform the result of the judgment to the driver through an amplifier 172 of the voice management module 170. Other detailed functions of the first processor 150 will be illustrated along with the operation of the safe driving system having a function of detecting HRV later.

The power module 160 is used to provide power required for operation to the HRV detecting module 110, the display interface module 120, the first internal wireless communication module 130, control button 140, first processor 150 and voice management module 170. In practice, power module 160 should be a direct current power supply module. Preferably, it is a removable secondary battery module, such as lithium-ion polymer batteries.

The voice management module 170 is connected to the first processor 150. It can send out and receives voice messages. The voice management module 170 includes a microphone 171 and the amplifier 172. Functions of the microphone 171 are converting voice into digital data, and sending out the digital data externally via the first processor 150, the first internal wireless communication module 130, the second internal wireless communication module 230, the second processor 250 and the mobile communication module 210. The microphone 171 may be an embedded microphone. The amplifier 172 is used to convert the digital data sent from the mobile communication module 210, through the second processor 250, the second internal wireless communication module 230, the first internal wireless communication module 130 and the first processor 150 into voice and amplify the voice. The amplifier 172 may be a mini speaker.

Figure 2:
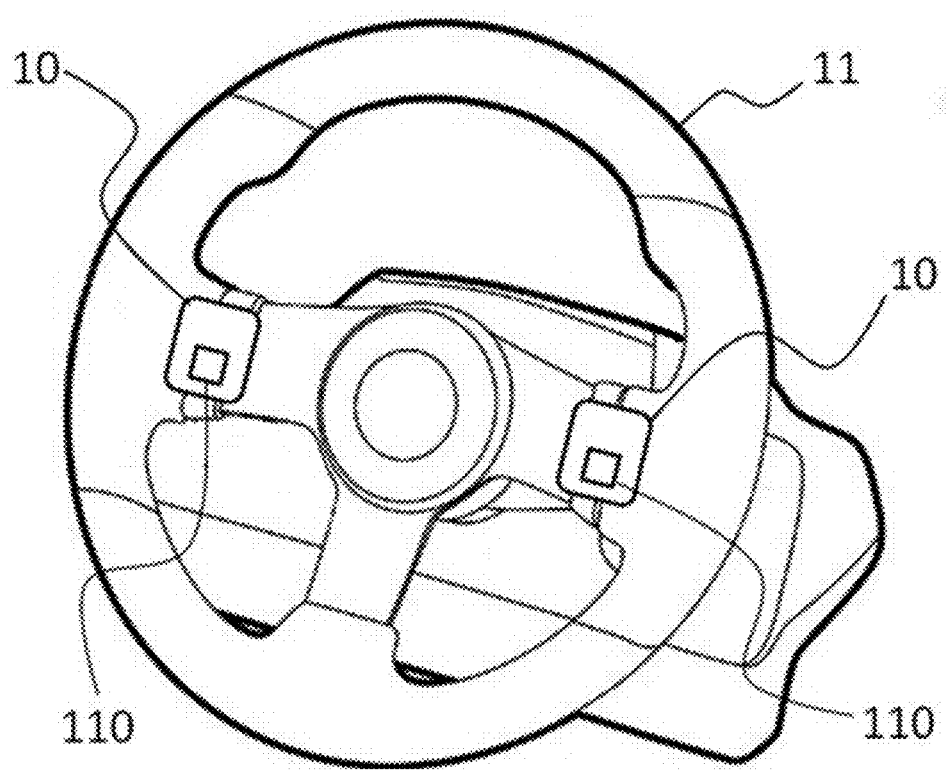
FIG. 2 is a schematic diagram showing a detection display unit connected to a steering wheel.
Figure 3:
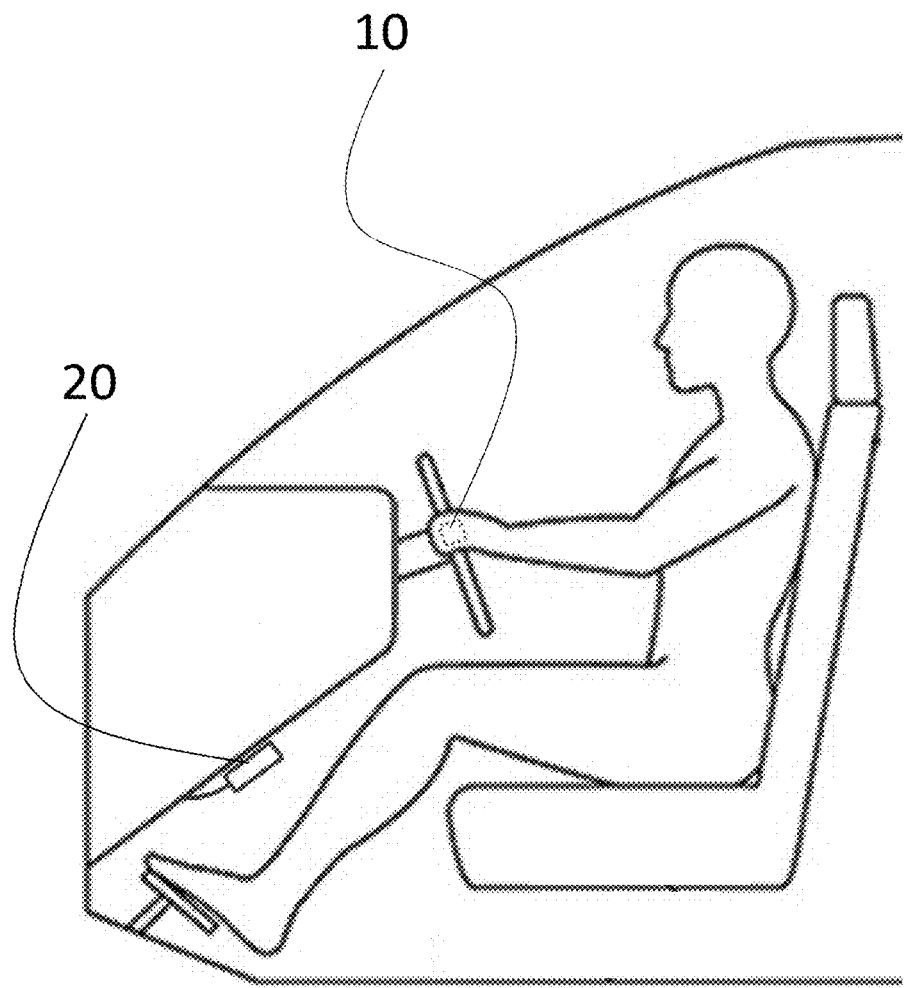
FIG. 3 is a schematic diagram showing installed locations of a detection display unit and a main control host.

Please see FIG. 2. It is a schematic diagram showing the detection display unit 10 is mounted on a steering wheel 11. As mentioned above, the number of the detection display unit 10 is not restricted to one. In the present embodiment, two detection display units 10 are mounted on the steering wheel 11. One detection display unit 10 is mounted on a left hand grip of the steering wheel 11 close to the fingers for touching, so that when a driver uses his left hand to hold the steering wheel 11, his left thumb is able to touch the HRV detecting module 110 of the detection display unit 10 to process detection. Similarly, the other detection display unit 10 is mounted on a right hand grip of the steering wheel 11 close to the fingers for touching, so that when a driver uses his right hand to hold the steering wheel 11, his right thumb is able to touch the HRV detecting module 110 of the detection display unit 10 to process detection. The description above is only an example of combination of the detection display unit 10 and the steering wheel 11. Locations of the steering wheel 11 suitable for connecting devices, as long as any finger or the palm can touch the HRV detecting module 110, are all in the scope of applications of the detection display unit 10 claimed by the present invention.

Please see FIG. 1 again. The mobile communication module 210 is installed with a SIM (Subscriber Identity Module, not shown) for sending and receiving messages through a mobile network 30. Hardware communicates with the mobile communication module 210 may be a mobile device 310, such as a smartphone, installed with an APP 315 interpreting said warning message and vehicle identification number. It may be a specific transceiver 320; it is a device for the public authorities, e.g. the police, to detect if drivers' physical and mental states are suitable for driving. Hardware of the specific transceiver 320 is specified to receive messages from the mobile communication module 210 or the second internal wireless communication module 230. The detection display unit 10 is able to make or answer a phone call through the mobile communication module 210. It can also input and receive voice through voice management module 170.

The satellite navigation system module 220, as illustrated in FIG. 1, is used to receive satellite signals from a satellite 40 to calculate location and speed information of the main control host 20. Satellite navigation system for the satellite navigation system module 220 may be, but not limited to Global Positioning System (GPS), GLONASS, Beidou satellite navigation system or Galileo satellite navigation system. Since the technology each satellite navigation system utilizes is different from others, the satellite navigation system module 220 may include one or more communication sub-modules for one or more satellite navigation systems. It is not restricted by the present invention. The location information is represented by a set of coordinates of the surface location after calculation, such as (25° 01'02.4"N; 121° 32'15.2"E).

The second internal wireless communication module 230 is paired with and wirelessly connected to the first internal wireless communication module 130. It can also pair and connect to the specific transceiver 320. Functions of the second internal wireless communication module 230 are the same as that of the first internal wireless communication module 130. It is not repeated here.

The storing module 240 can be used to store at least one mobile phone number, a vehicle identification number of the vehicle, a number of newest recorded HRV values from the first internal wireless communication module 130, and HRV values patterns (values) of the vehicle owner and a number of users authorized by the vehicle owner to use the vehicle. Therefore, the HRV can be used as a biometric technology to identify whether the vehicle owner is driving the vehicle, or the one other than the vehicle owner is authorized by the vehicle owner to use the vehicle. Because there are many sets of patterns of HRV stored, the safe driving system having a function of detecting HRV is able to allow limited number of people to drive the vehicle, further implementing a function of anti-theft for vehicles. The mobile phone numbers mentioned above may belong to the vehicle owner, a number of authorized users often using the vehicle or the one in charge of managing the vehicle. The newest recorded HRV values are used as proofs recorded in advance for disputes possibly happen in the future. For example, when sobriety test, the record can be a data to auxiliarily prove whether the driver is drinking before driving. In practice, the storing module 240 may be a NAND Flash module, or a DRAM (Dynamic Random Access Memory) module.

The second processor 250 is connected to the mobile communication module 210, the satellite navigation system module 220, the second internal wireless communication module 230, the storing module 240 and the alarm module 290, for operating said connected objects, judging if a data is stored in the storing module 240, and sending out the warning message, the location and speed information of the vehicle and the vehicle identification number from the first internal wireless communication module 130 to the mobile network 30 (or the specific transceiver 320) and the mobile device 310 via the mobile communication module 210. It also pairs and connects the second internal wireless communication module 230 and the specific transceiver 320. Detailed functions of the second processor 250 will be illustrated along with the operation of the safe driving system having a function of detecting HRV.

The vehicle power module 260 is connected to the power supply of the vehicle (direct current source, not shown), for receiving the power from the vehicle and providing the power to the power management module 280. The secondary power module 270 may be a set of secondary batteries, for storing and supplying power to the main control host 20. The power management module 280 is connected to the mobile communication module 210, the satellite navigation system module 220, the second internal wireless communication module 230, the storing module 240, the second processor 250, the vehicle power module 260, the secondary power module 270 and the alarm module 290, for controlling the power from the vehicle power module 260 for the operation of each module in the main control host 20. It can also provide the power from the secondary power module 270 to maintain the operation of the main control host 20 when an abnormal power failure occurs between the vehicle power module 260 and the power supply of the vehicle (destroyed by thieves).

The alarm module 290 is capable of making alarming sounds to remind the driver of safety driving. In practice, is can be a buzzer.

The main control host 20 can be installed on the location of the fuse box of the vehicle and connect the vehicle power module 260 of the main control host 20 to the power supply of the vehicle. When the power supply of the vehicle initiates, power is provided to the vehicle power module 260 at the same time. At this moment, the second internal wireless communication module 230 of the main control host 20 will detect if there are the first internal wireless communication modules 130 around for pairing and connecting. The safe driving system having a function of detecting HRV starts to function. The operation of the safe driving system having a function of detecting HRV is described in details below.

Figure 4:
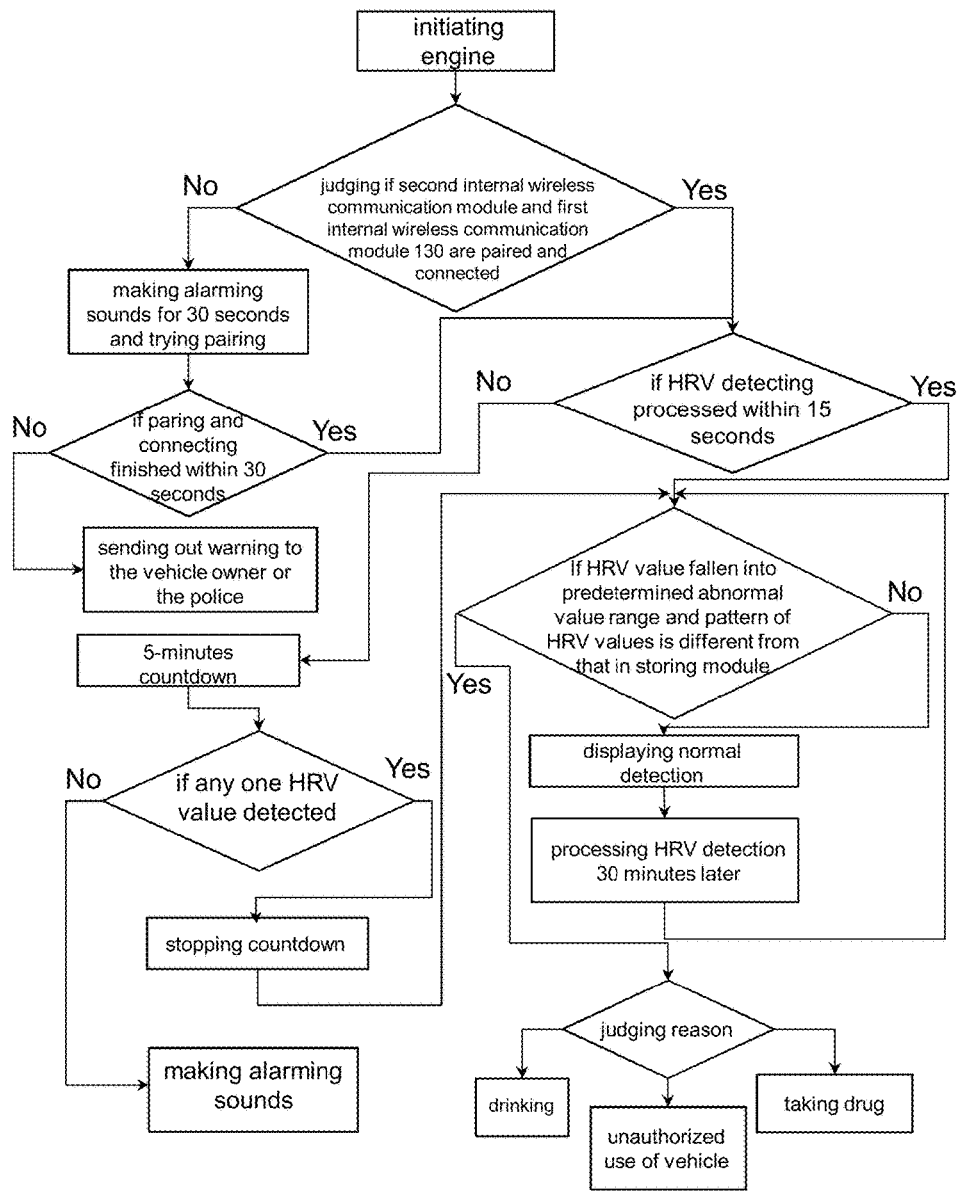
FIG. 4 is a flowchart of operation of the safe driving system having a function of detecting HRV.

Please see FIG. 4. It is a flowchart of operation of the safe driving system having a function of detecting HRV. After the driver starts the engine, the second processor 250 judges if the second internal wireless communication module 230 and the first internal wireless communication module 130 are paired and connected. When the second processor 250 judges the second internal wireless communication module 230 and the first internal wireless communication module 130 are not paired and connected, the alarm module 290 makes alarming sounds for 30 seconds. The alarming sounds not only remind the driver of checking whether the detection display unit 10 is off or out of order, but there is sufficient power from the power module 160. Meanwhile, it can frighten thieves. During the 30 seconds of alarming sounds, the second internal wireless communication module 230 still keeps detecting and tries to pair and connect to the first internal wireless communication module 130 in other detection display unit 10 around if any. If paring and connecting are not finished within 30 seconds, the second processor 250 sends out an alert message to the vehicle owner or the police via the mobile communication module 210 to inform them that the vehicle might be stolen. If paring and connecting are finished within 30 seconds, the HRV detecting module 110 waits for 15 seconds for the driver to process HRV detecting. This job must be processed after the second internal wireless communication module 230 and the first internal wireless communication module 130 are paired and connected.

If the driver processes HRV detecting within 15 seconds the HRV detecting module 110 waits, the first processor 150 judges whether the HRV value falls into the predetermined abnormal value range, and the second processor 250 judges if the pattern of the HRV values is different from that of the vehicle owner and a plurality of users authorized by the vehicle owner in the storing module 240. If the HRV value detected by the HRV detecting module 110 and judged by the first processor 150 is "no", it means the detected value doesn't fall into the predetermined abnormal value range, and the display interface module 120 displays a normal detection message. The HRV detecting module 110 processes another HRV detecting within 30 minutes to the driver to judge if the HRV value falls into the predetermined abnormal value range for ensuring that the driver is physically and mentally fit while driving. Otherwise, if the driver doesn't processes HRV detecting within 15 seconds the HRV detecting module 110 waits, the first processor 150 initiates a 5-minutes countdown. Detecting HRV value repeatedly every 30 minutes is to prevent the driver from drinking, taking drugs or mental fatigue while driving, resulting in a bad state of mind and body, not suitable for driving.

If the HRV value falls into the predetermined abnormal value range, a reason that the HRV value fallen into the predetermined abnormal value range is caused by drinking, fatigue or taking drug is judged by the first processor 150 through the HRV detecting module 110. if the pattern of the HRV values of the driver is different from that of the vehicle owner or a number of authorized users in the storing module 240, the first processor 150 judges that the vehicle may be stolen without permission. If the HRV value fallen into the predetermined abnormal value range is caused by drinking, the HRV detecting module 110 sends out a drunk driving warning message to display on the display interface module 120 to warn the driver to stop by the roadside and shut down the engine. The drunk driving warning message may be a red light, or a text informing the driver that he might drink while driving and stop by the roadside. The alarm module 290 makes alarming sounds every 5 minutes. The display interface module 120 is continuously showing the message of stopping and shutting down the engine. The drunk driving warning message is passed to the second internal wireless communication module 230 via the first internal wireless communication module 130, further sent to the police or fire department reporting system, the specific transceiver 320 of patrol police officers within 5 meters around the vehicle, a mobile device of the vehicle owner, or the mobile device 310 installed with the APP 315 interpreting the drunk driving warning message, emergency message and the vehicle identification number, along with the emergency message, the location of the vehicle (location information), the speed of the vehicle and the vehicle identification number through the second processor 250 and the mobile communication module 210. The mobile device 310 makes a warning sound and shows the vehicle identification number, warning people around the vehicle to keep away and prevent danger. Meanwhile, the patrol police officers can use the specific transceiver 320 to detect the drunk driving warning message sent from the main control host 20 within 5 meters around the vehicle. If necessary, they can inspect the vehicle. In addition, if the SIM card has problems or been suspended due to overdue payment, the mobile communication module 210 of the main control host 20 can still automatically dial 110 (a service without SIM) to inform the police reporting system about the drunk driving warning message, location information and the vehicle identification number.

If the HRV value fallen into the predetermined abnormal value range is caused by taking drug, the HRV detecting module 110 sends out an drug taking warning message to display on the display interface module 120 to warn the driver to stop by the roadside and shut down the engine. The drug taking warning message may be a red light or a text informing the driver that he might take drug while driving and stop by the roadside. The alarm module 290 makes alarming sounds every 5 minutes. The display interface module 120 is continuously showing the message of stopping and shutting down the engine. The drug taking warning message is passed to the second internal wireless communication module 230 via the first internal wireless communication module 130, further sent to the police reporting system, the specific transceiver 320 of patrol police officers within 5 meters around the vehicle, or the mobile device 310 installed with the APP 315 interpreting the drug taking warning message and the vehicle identification number, along with the location of the vehicle and the vehicle identification number through the second processor 250 and the mobile communication module 210. Therefore, similarly, the mobile device 310 makes a warning sound and shows the vehicle identification number, warning people around the vehicle to keep away. The patrol police officers can use the specific transceiver 320 to detect the drug taking warning message sent from the main control host 20 within 5 meters around the vehicle. If necessary, they can inspect the vehicle. In addition, if the SIM card has problems or been suspended due to overdue payment, the mobile communication module 210 of the main control host 20 can still automatically dial 110 to inform the police reporting system about the drug taking warning message, location information and the vehicle identification number.

If the HRV value fallen into the predetermined abnormal value range is caused by fatigue, the HRV detecting module 110 sends out an fatigue driving warning message to display on the display interface module 120 to warn the driver to stop by the roadside and shut down the engine. The fatigue driving warning message may be a red light, or a text informing the driver that he might be fatigue driving and stop by the roadside. The alarm module 290 makes alarming sounds every 5 minutes. The display interface module 120 is continuously showing the message of stopping and shutting down the engine. The fatigue driving warning message is passed to the second internal wireless communication module 230 via the first internal wireless communication module 130, further sent to the police reporting system, the specific transceiver 320 of patrol police officers within 5 meters around the vehicle, or the mobile device 310 installed with the APP 315 interpreting the fatigue driving warning message and the vehicle identification number, along with the location of the vehicle and the vehicle identification number through the second processor and the mobile communication module. Therefore, similarly, the mobile device 310 makes a warning sound and shows the vehicle identification number, warning people around the vehicle to keep away. The patrol police officers can use the specific transceiver 320 to detect the fatigue driving warning message sent from the main control host 20 within 5 meters around the vehicle. If necessary, they can inspect the vehicle. In addition, if the SIM card has problems or been suspended due to overdue payment, the mobile communication module 210 of the main control host 20 can still automatically dial 110 to inform the police reporting system about the fatigue driving warning message, location information and the vehicle identification number.

If the HRV detecting module 110 finds out that the pattern of the HRV values is different from that in the storing module 240, the HRV detecting module 110 sends out an unauthorized driving warning message to display on the display interface module 120. The unauthorized driving warning message may be a yellow light or a text showing to the driver that he is not authorized to use the vehicle. The unauthorized driving warning message is passed to the second internal wireless communication module 230 via the first internal wireless communication module 130, further sent to a mobile device of the vehicle owner, the specific transceiver 320 of patrol police officers within 5 meters around the vehicle, the mobile device 310 installed with the APP 315 interpreting the unauthorized driving warning message, or a number of mobile devices owned by users authorized by the vehicle owner, along with the location of the vehicle through the second processor 250 and the mobile communication module 210. Thus, both the vehicle owner and the police can control the situation of the stolen vehicle. A mobile device of the vehicle owner must be installed with the APP 315 to be informed and shown the location information of the vehicle. Meanwhile, because the vehicle owner can talk to the driver, it is able to clarify who is the driver not authorized to drive the vehicle by the vehicle owner.

As mentioned above, if any one HRV value (no matter an authorized or unauthorized personnel uses the safe driving system having a function of detecting HRV to drive the vehicle) is detected by the HRV detecting module 110 within the 5-minutes countdown, the first processor 150 stops the 5-minutes countdown, and the HRV detecting module 110 judges if the HRV value falls into the predetermined abnormal value range or not. The judging process keeps repeating. However, if no HRV value is detected by the HRV detecting module 110 within the 5-minutes countdown, the HRV detecting module 110 sends out a no-HRV-detected driving warning message to display on the display interface module to warn the driver to stop by the roadside and shut down the engine. The no-HRV-detected driving warning message may be a text advising the driver to stop by the roadside and shut down the engine, or process detection of HRV for traffic safety. The alarm module 290 makes alarming sounds every 1 minute. The display interface module 120 keeps showing message to ask the driver to process detection of HRV. The no-HRV-detected driving warning message is passed to the second internal wireless communication module 230 via the first internal wireless communication module 130, further sent to the police reporting system, the specific transceiver 320 of patrol police officers within 5 meters around the vehicle, or the mobile device 310 installed with the APP 315 interpreting the no-HRV-detected driving warning message and the vehicle identification number, along with the location of the vehicle and the vehicle identification number through the second processor 250 and the mobile communication module 210. Similarly, the mobile device 310 makes a warning sound and shows the no-HRV-detected driving warning message and the vehicle identification number, warning people around the vehicle to keep away. The patrol police officers can use the specific transceiver 320 to detect the no-HRV-detected driving warning message sent from the main control host 20 within 5 meters around the vehicle. If necessary, they can inspect the vehicle. In addition, if the SIM card has problems or been suspended due to overdue payment, the mobile communication module 210 of the main control host 20 can still automatically dial 110 to inform the police reporting system about the no-HRV-detected driving warning message, location information and the vehicle identification number.

According to the spirit of the present invention, if the driver suddenly feels discomfort during driving or is injured in a car accident so that he cannot drive normally, the safe driving system having a function of detecting HRV can provide a function of urgent help. According to FIG. 4, steps after "yes" of "judging if second internal wireless communication module and first internal wireless communication module 130 are paired and connected", namely, after the detection display unit 10 and the main control host 20 finish pairing and connecting, no matter the driver complete detection of HRV or not, if the control button is pressed over 8 seconds, the first processor 150 sends out an emergency message. The emergency message is passed to the second internal wireless communication module 230 via the first internal wireless communication module 130, further sent to the fire department reporting system without the help of the SIM card via the free call of 119, the specific transceiver 320 of patrol police officers within 5 meters around the vehicle, or the mobile device 310 installed with an APP 315 interpreting the emergency message and the vehicle identification number, along with the location of the vehicle and the vehicle identification number through the second processor 250 and the mobile communication module 210. Meanwhile, the driver can talk with the ambulance staff through the voice management module 170 to inform him of the current situation. The ambulance staff comes to the scene to rescue the driver with their best according to the location information and vehicle identification number.

In addition, in order to remind the driver of speeding violation, the safe driving system having a function of detecting HRV provides a procedure. The second processor 250 utilizes location information received by the satellite navigation system module 220 to calculate the speed of the vehicle after the engine of the vehicle is initiated. If the second processor 250 finds that the speed of the vehicle is higher than a maximum speed limit of a road where the vehicle runs to a certain percentage, e.g., the vehicle travels over the national highway for more than 10% of the speed limit of 110 km/h, or 121 km/h, and the speed of the vehicle keeps for more than 20 seconds, the second processor 250 sends out an speeding violation message, the location of the vehicle, the speed of the vehicle and the vehicle identification number to the police reporting system or the specific transceiver 320 of patrol officers within 5 meters around the vehicle via the mobile communication module, and stores details of speeding in the storing module 240 for the police to verify. Meanwhile, the alarm module 290 makes a 1-minute warning sound to remind the driver to slow down immediately. If the driver does not want to slow down and keeps speeding for more than 1 minute, the alarm module 290 changes to make a 10-seconds warning sound, every 20 seconds.

Last, in order to prevent collisions between vehicles, the safe driving system having a function of detecting HRV provide a method. Assume there are two vehicles (vehicle A and vehicle B) both equipped with the safe driving system having a function of detecting HRV. Under the condition that the vehicle power is turned on, the main control hosts 20 of vehicle A and vehicle B can use the mobile communication module 210 of the main control host 20 in respective vehicle to detect whether the distance between two vehicles is less than 100 meters. If vehicle B comes close to vehicle A with a higher speed, and the distance between two vehicles is less than 100 meters, the mobile communication module 210 of vehicle A will receive the location and the speed of vehicle B sent from the mobile communication module 210 of vehicle B. The location and the speed of vehicle B and that of vehicle A are sent to the second processor 250 of vehicle A for comparing and calculating the location information and speeds. If it is found that the speed of vehicle B and its moving direction might cause collision of the vehicles, the alarm module 290 in vehicle A will make a sound immediately and the display interface module 120 shows message to warn the driver of vehicle A to make emergency action to protect himself. Similarly, the alarm module 290 in vehicle B will also make a sound and the display interface module 120 shows message to warn the driver of vehicle B to slow down immediately and pay attention to maintain a proper distance with vehicle A in the front. Thus, collision of two vehicles can be prevented.

While the invention has been described in terms of what is presently considered to be the most practical and preferred embodiments, it is to be understood that the invention needs not be limited to the disclosed embodiments. On the contrary, it is intended to cover various modifications and similar arrangements included within the spirit and scope of the appended claims, which are to be accorded with the broadest interpretation so as to encompass all such modifications and similar structures.

What is claimed is:

1. A safe driving system having function of detecting heart rate variability, comprising:
    a detection display unit, comprising:
        a Heart Rate Variability (HRV) detecting module, for detecting and outputting a HRV value of a vehicle driver, and when the detected HRV value fallen into a predetermined abnormal value range, sending out a corresponding warning message;
        a display interface module, for displaying the warning message or a light or a text corresponding to the warning message;
        a first internal wireless communication module, for sending and receiving wireless signals;
        a control button, touched to control the display interface module and sending out an emergency message;
        a first processor, connected to the HRV detecting module, the display interface module, the first internal wireless communication module and the control button, for operating said connected modules and button, and sending out the warning message, the emergency message and records of HRV values via the first internal wireless communication module; and
        a power module, for providing power required for operation to the HRV detecting module, the display interface module, the first internal wireless communication module, the control button, and the first processor; and
    a main control host, comprising:
        a mobile communication module, installed with a Subscriber Identity Module (SIM), for sending and receiving messages through a mobile network;
        a satellite navigation system module, for receiving satellite signals to calculate location and speed information of the main control host;
        a second internal wireless communication module, paired with and wirelessly connected to the first internal wireless communication module, for sending and receiving wireless signals;
        a storing module, for storing HRV values patterns of a vehicle owner and a plurality of users authorized by the vehicle owner to use the vehicle, at least one mobile phone number, a vehicle identification number of the vehicle, and a plurality of newest recorded HRV values from the first internal wireless communication module; and
        a second processor, connected to the mobile communication module, the satellite navigation system module, the second internal wireless communication module and the storing module, for operating said connected modules, judging if a data is stored in the storing module, and sending out the warning message, the emergency message, the location and speed information and the vehicle identification number from the first internal wireless communication module to a specific external receiver via the mobile communication module.

2. The safe driving system having function of detecting heart rate variability according to claim 1, wherein the detection display unit further comprises:
    a voice management module, connected to the first processor, for sending out and receiving voice messages, comprising:
        a microphone, for converting voice into digital data, and sending out the digital data externally via the first processor, the first internal wireless communication module, the second internal wireless communication module, the second processor and the mobile communication module; and
        an amplifier, for converting digital data sent from the mobile communication module, through the second processor, the second internal wireless communication module, the first internal wireless communication module and the first processor into voice and amplifying the voice.

3. The safe driving system having function of detecting heart rate variability according to claim 2, wherein the detection display unit is able to make or answer a phone call through the mobile communication module of the main control host, and input and receive voice through the voice management module.

4. The safe driving system having function of detecting heart rate variability according to claim 2, wherein the first processor utilizes the HRV value of the vehicle driver detected by the HRV detecting module to judge if the driver is suitable for driving or not, and inform the driver about the result of judgment through the amplifier of the voice management module.

5. The safe driving system having function of detecting heart rate variability according to claim 1, wherein the predetermined abnormal value range is a range of HRV values measured from human experiments under fatigue, lack of sleep, taking drug, drinking or acute illness resulting in inability to drive the vehicle properly.

6. The safe driving system having function of detecting heart rate variability according to claim 1, wherein the first internal wireless communication module and the second internal wireless communication module are Bluetooth modules or Near Field Communication (NFC) modules.

7. The safe driving system having function of detecting heart rate variability according to claim 1, wherein the warning message, the emergency message, the location of the vehicle, the speed of the vehicle and the vehicle identification number are sent to the police or fire department reporting system, a specific transceiver of patrol police officers, a mobile device of the vehicle owner, or a mobile device installed with an APP interpreting the warning message, the emergency message and the vehicle identification number.

8. The safe driving system having function of detecting heart rate variability according to claim 5, wherein the main control host further comprises an alarm module capable of making alarming sounds.

9. The safe driving system having function of detecting heart rate variability according to claim 8, after the vehicle engine is started, the second processor further judges if the second internal wireless communication module and the first internal wireless communication module are paired and connected; when the second processor judges the second internal wireless communication module and the first internal wireless communication module are not paired and connected, the alarm module makes alarming sounds for 30 seconds and the second internal wireless communication module keeps detecting and tries to pair and connect to the first internal wireless communication module in other detection display unit; if paring and connecting are not finished within 30 seconds, the second processor sends out an alert message to the vehicle owner or the police via the mobile communication module; if paring and connecting are finished within 30 seconds, the HRV detecting module waits for 15 seconds for the driver to process HRV detecting.

10. The safe driving system having function of detecting heart rate variability according to claim 9, if the driver processes HRV detecting within 15 seconds, the first processor judges whether the HRV value falls into the predetermined abnormal value range, and the second processor judges if the pattern of the HRV values is different from that of the vehicle owner and a plurality of users authorized by the vehicle owner in the storing module; if the driver doesn't processes HRV detecting within 15 seconds, the first processor further initiates a 5-minutes countdown.

11. The safe driving system having function of detecting heart rate variability according to claim 10, after detection of the HRV detecting module, if the HRV value doesn't fall into the predetermined abnormal value range, the display interface module displays a normal detection message, and the HRV detecting module processes another HRV detecting within 30 minutes to the driver to judge if the HRV value falls into the predetermined abnormal value range for ensuring that the driver is physically and mentally fit while driving.

12. The safe driving system having function of detecting heart rate variability according to claim 10, if the HRV value falls into the predetermined abnormal value range, a reason that the HRV value fallen into the predetermined abnormal value range is caused by drinking, fatigue or taking drug is judged by the first processor through the HRV detecting module.

13. The safe driving system having function of detecting heart rate variability according to claim 12, if the HRV value fallen into the predetermined abnormal value range is caused by drinking, the HRV detecting module sends out a drunk driving warning message to display on the display interface module to warn the driver to stop by the roadside and shut down the engine, the alarm module makes alarming sounds every 5 minutes, and the drunk driving warning message is passed to the second internal wireless communication module via the first internal wireless communication module, further sent to the police reporting system, a specific transceiver of patrol police officers within 5 meters around the vehicle, or a mobile device installed with an APP interpreting the drunk driving warning message and the vehicle identification number, along with the location of the vehicle and the vehicle identification number through the second processor and the mobile communication module.

14. The safe driving system having function of detecting heart rate variability according to claim 12, if the HRV value fallen into the predetermined abnormal value range is caused by taking drug, the HRV detecting module sends out an drug taking warning message to display on the display interface module to warn the driver to stop by the roadside and shut down the engine, the alarm module makes alarming sounds every 5 minutes, and the drug taking warning message is passed to the second internal wireless communication module via the first internal wireless communication module, further sent to the police reporting system, a specific transceiver of patrol police officers within 5 meters around the vehicle, or a mobile device installed with an APP interpreting the drug taking warning message and the vehicle identification number, along with the location of the vehicle and the vehicle identification number through the second processor and the mobile communication module.

15. The safe driving system having function of detecting heart rate variability according to claim 12, if the HRV value fallen into the predetermined abnormal value range is caused by fatigue, the HRV detecting module sends out an fatigue driving warning message to display on the display interface module to warn the driver to stop by the roadside and shut down the engine, the alarm module makes alarming sounds every 5 minutes, and the fatigue driving warning message is passed to the second internal wireless communication module via the first internal wireless communication module, further sent to the police reporting system, a specific transceiver of patrol police officers within 5 meters around the vehicle, or a mobile device installed with an APP interpreting the fatigue driving warning message and the vehicle identification number, along with the location of the vehicle and the vehicle identification number through the second processor and the mobile communication module.

16. The safe driving system having function of detecting heart rate variability according to claim 12, if the pattern of the HRV values is different from that in the storing module, the HRV detecting module sends out an unauthorized driving warning message to display on the display interface module, and the unauthorized driving warning message is passed to the second internal wireless communication module via the first internal wireless communication module, further sent to a mobile device of the vehicle owner, a specific transceiver of patrol police officers within 5 meters around the vehicle, a mobile device installed with an APP interpreting the unauthorized driving warning message, or a plurality of mobile devices owned by users authorized by the vehicle owner, along with the location of the vehicle through the second processor and the mobile communication module.

17. The safe driving system having function of detecting heart rate variability according to claim 10, if any one HRV value is detected by the HRV detecting module within the 5-minutes countdown, the first processor stops the 5-minutes countdown, and the HRV detecting module judges if the HRV value falls into the predetermined abnormal value range or not.

18. The safe driving system having function of detecting heart rate variability according to claim 10, if no HRV value is detected by the HRV detecting module within the 5-minutes countdown, the HRV detecting module sends out a no-HRV-detected driving warning message to display on the display interface module to warn the driver to stop by the roadside and shut down the engine, the alarm module makes alarming sounds every 1 minute, the no-HRV-detected driving warning message is passed to the second internal wireless communication module via the first internal wireless communication module, further sent to the police reporting system or a specific transceiver of patrol police officers within 5 meters around the vehicle along with the location of the vehicle and the vehicle identification number through the second processor and the mobile communication module.

19. The safe driving system having function of detecting heart rate variability according to claim 1, if the control button is pressed over 8 seconds, the first processor sends out the emergency message, and the emergency message is passed to the second internal wireless communication module via the first internal wireless communication module, further sent to the fire department reporting system, a specific transceiver of patrol police officers within 5 meters around the vehicle, or a mobile device installed with an APP interpreting the emergency message and the vehicle identification number along with the location of the vehicle and the vehicle identification number through the second processor and the mobile communication module.

20. The safe driving system having function of detecting heart rate variability according to claim 1, wherein the second processor utilizes location information received by the satellite navigation system module to calculate the speed of the vehicle after the engine of the vehicle is initiated.

21. The safe driving system having function of detecting heart rate variability according to claim 20, if the second processor finds that the speed of the vehicle is higher than a maximum speed limit of a road where the vehicle runs to a certain percentage and the speed of the vehicle keeps for more than 20 seconds, the second processor sends out an speeding violation message, the location of the vehicle, the speed of the vehicle and the vehicle identification number to the police reporting system or a specific transceiver of patrol police officers within 5 meters around the vehicle via the mobile communication module, and stores details of speeding in the storing module.

22. The safe driving system having function of detecting heart rate variability according to claim 8, wherein the main control host further comprises:
 a vehicle power module, connected to a power supply of the vehicle;
 a secondary power module, for storing and supplying power; and
 a power management module, connected to the mobile communication module, the satellite navigation system module, the second internal wireless communication module, the storing module, the second processor, the vehicle power module, the secondary power module and the alarm module, for controlling the power from the vehicle power module for the operation of each module in the main control host, and providing the power from the secondary power module to maintain the operation of the main control host when an abnormal power failure occurs between the vehicle power module and the power supply of the vehicle.

23. The safe driving system having function of detecting heart rate variability according to claim 1, wherein the detection display unit further comprises: the power module, for providing the power for the operation of the HRV detecting module, the display interface module, the first internal wireless communication module, the control button, the first processor and a voice management module.

* * * * *